(12) United States Patent
Delnevo et al.

(10) Patent No.: US 8,021,319 B2
(45) Date of Patent: Sep. 20, 2011

(54) EXTRACORPOREAL BLOOD SET

(75) Inventors: Annalisa Delnevo, Sant'Agata Bolognese (IT); Roberto Neri, Mirandola (IT)

(73) Assignee: Gambro Lundia AB, Lund (SE)

( * ) Notice: Subject to any disclaimer, the term of this patent is extended or adjusted under 35 U.S.C. 154(b) by 578 days.

(21) Appl. No.: 12/090,829

(22) PCT Filed: Oct. 27, 2005

(86) PCT No.: PCT/IB2005/003211
§ 371 (c)(1),
(2), (4) Date: Apr. 18, 2008

(87) PCT Pub. No.: WO2007/049092
PCT Pub. Date: May 3, 2007

(65) Prior Publication Data
US 2008/0214981 A1    Sep. 4, 2008

(51) Int. Cl.
*A61M 37/00* (2006.01)
(52) U.S. Cl. ............ 604/6.16; 604/6.06; 604/6.09; 604/6.1; 604/6.11
(58) Field of Classification Search ............ 604/4.01, 604/5.01, 5.04, 6.09, 6.1, 6.11, 6.16
See application file for complete search history.

(56) References Cited

U.S. PATENT DOCUMENTS

| | | | |
|---|---|---|---|
| 3,916,892 A | 11/1975 | Latham, Jr. | |
| 4,334,535 A | 6/1982 | Wilson | |
| 4,850,995 A * | 7/1989 | Tie et al. | 604/6.02 |
| 5,360,395 A | 11/1994 | Utterberg | |
| 5,364,377 A | 11/1994 | O'Neil | |
| 5,650,071 A | 7/1997 | Brugger et al. | |
| 5,776,091 A | 7/1998 | Brugger et al. | |
| 6,387,069 B1 * | 5/2002 | Utterberg | 604/4.01 |
| 6,454,736 B1 | 9/2002 | Ludt et al. | |
| 6,770,049 B2 | 8/2004 | Ludt et al. | |
| 7,226,538 B2 | 6/2007 | Brugger et al. | |
| 2002/0151834 A1 | 10/2002 | Utterberg | |
| 2004/0222139 A1 | 11/2004 | Brugger et al. | |
| 2004/0236286 A1 | 11/2004 | Klein | |

FOREIGN PATENT DOCUMENTS

| | | |
|---|---|---|
| DE | 9201329 U | 8/1992 |
| DE | 4203069 | 8/1993 |
| EP | 0663216 | 7/1995 |
| FR | 2704150 | 10/1994 |
| WO | WO9110861 | 7/1991 |
| WO | WO9640320 | 12/1996 |
| WO | W003006139 | 1/2003 |
| WO | 2007/047845 A2 | 4/2007 |

* cited by examiner

*Primary Examiner* — Leslie R Deak
(74) *Attorney, Agent, or Firm* — Pearne & Gordon LLP

(57) ABSTRACT

A blood set comprises an arterial line having a patient end provided with a multiport connector (14) having first port (15) connected to a blood transport tube (13), a second port (16) bearing a male luer connector for connecting to a vascular access device (17), and a third port (18) connected to a service tube (20) terminating with female luer connector (23) for connection with a priming liquid supply line. The blood set operates rapidly and with a small risk of contamination for the patient.

9 Claims, 3 Drawing Sheets

EXTRACORPOREAL BLOOD SET

BACKGROUND OF THE INVENTION

The invention relates to a set for extracorporeal circulation of blood and to a procedure for filling and rinsing the set with a physiological solution.

Specifically, though not exclusively the invention can be usefully applied in performing a priming of an extracorporeal circuit used in an apparatus for extracorporeal blood treatment, such as for example a dialysis machine, a hemoperfusion device, a blood oxygenator, a blood component separator, and the like.

As is well known, before performing a dialysis operation, the extracorporeal blood circuit of the dialysis equipment must be filled with an isotonic fluid, normally a sodium chloride solution with a concentration of 155 mmol/l. This procedure, normally known as priming, has the objective of rinsing the circuit and removing the air and any particles and sterilizing fluid left in the circuit.

The prior art includes a priming set predisposed to supply the isotonic solution to the extracorporeal blood circuit both during the priming stage, before treatment, and during the treatment itself, and also following treatment. During treatment (for example during a dialysis session) the isotonic solution can be injected into the extracorporeal blood, for example in a case of patient hypertension or as a dilutor during administration of a medicinal substance. The isotonic solution can also be used in treatment for the movement of the extracorporeal blood being returned to the patient.

The prior art includes an extracorporeal circuit (for example a dialysis set) which is made in two parts, an arterial part and a venous part, each of which has a first end provided with a connector to the patient for connection to a vascular access, and a second end having a device connector for connection to a blood treatment device (dialyser). During treatment the arterial part receives the blood from the patient and sends it to the blood treatment device, while the venous part receives the treated blood from the device and returns it to the patient. Normally the arterial part includes a branch tube for administration of the saline, which tube typically terminates in a female luer connector for connection to an end of the priming set. During the priming procedure the extracorporeal circuit is connected to the blood treatment device and the priming set is connected to the branch tube. In a first priming stage the saline fills the arterial zone comprised between the patient connector and the branch tube. During this stage the patient connector is open to enable expulsion of air from the circuit. In a second stage the rest of the circuit is filled up to the patient end of the venous part. Between the first and the second stages the patient connector of the arterial line must be closed and manual clamps are activated to direct the saline in the right direction. This known priming process is however very long and laborious as it requires two successive stages which are further separated by a stage of clamping and unclamping. Also, as the interruption of the first stage must be done in a timely fashion in order to avoid excessive exiting of liquid from the patient connector, the operator must be especially focused on the task in hand.

In another known priming procedure the patient end of the arterial line is connected directly to a bag of saline, after which the saline can fill the whole extracorporeal circuit up to the patient connection of the venous line in a single stage. Thereafter the priming set is detached from the patient end of the arterial line and connected to the branch tube of the arterial line until the saline is ready to be used during treatment. As at the end of each priming procedure, and before starting treatment the arterial line has to be connected to the vascular access of the patient, in the case described herein the patient connection to the arterial line is exposed to risk of contamination as soon as the priming set is detached (and is therefore still wet) and before being connected to the patient.

U.S. Pat. No. 6,387,069 describes an extracorporeal blood transport set comprising a first branch line which branches off from a first branch point in an intermediate zone of the arterial line and which in a priming stage is connected to a source (a bag) of saline. The first branch line exhibits a second branch point to which a service connector is connected, directly or via a second branch line, which service connector is predisposed to be connected with the patient connector of the arterial line. U.S. Pat. No. 6,387,069 also describes a procedure for priming the above-cited extracorporeal blood transport set, according to which the patient connector of the arterial line is connected to the service connector in order to form a closed loop comprising: the service connector with, if present, the second branch line; the part of arterial line comprised between the patient connector and the first branch point; and the part of first branch line comprised between the first and second branch points. In this priming configuration the saline can perform the filling and rinsing of the part of arterial line comprised between the patient connection and the first branch point. This priming procedure also exhibits various drawbacks. Firstly the preliminary operation of connecting the patient connector to the service connector involves a risk of contamination of the arterial line which will then be connected to the patient. Secondly the transport set must be provided with a relatively complicated valve system, both in structural and practical terms, during the priming, because of the selective closure of the first branch line (between the first and second branch points) and the service connection (or the second branch line if present). Also, the presence of a service connection as well as the first branch line in itself represents a complication.

U.S. Pat. No. 6,770,049 discloses a blood set for extracorporeal blood circulation comprising an arterial line, a venous line, a priming inlet line which branches off from the arterial line, and a priming liquid return line which branches off from the venous line. U.S. Pat. No. 6,770,049 further describes a filling procedure of the blood set in which the inlet line of the priming liquid is connected at one end to a container of the priming liquid and at the other end to the priming liquid return line. The arterial patient end and the venous patient end are closed by respective security caps provided with a hydrophobic membrane which is permeable to gas but not to liquids. During the priming procedure, the air contained in the blood set is released through the hydrophobic membrane in order to enable complete filling of the blood set without the liquid's escaping. However, the use of special security caps has a negative effect on the cost of the blood set. Furthermore the priming procedure is complicated by the need for a stage of removing and discarding the security caps before setting up the blood set connection to the patient.

SUMMARY OF THE INVENTION

A main aim of the present invention is to provide a set for extracorporeal blood circulation which obviates the above-described limitations and drawbacks in the prior art.

A further aim of the invention is to provide a priming process for the blood set of the invention.

A further aim of the invention is to provide a process for terminating an extracorporeal blood treatment using the blood set of the invention.

An advantage of the invention is to realize a blood set which is constructionally simple and economical.

A further advantage is to enable a priming of an extracorporeal blood circuit with small and simple operations, reducing the time needed for readying the circuit before the extracorporeal treatment.

A further advantage is to reduce the risk of contamination of a patient or donor using a set for extracorporeal blood circulation. The risk of contamination is low with the blood set of the invention, for example because of the fact that the patient end has a connection port, destined to be connected with a vascular access device, which is not opened either before or during the priming, but stays closed off by the cap which seals it during the packing stage and which is opened only at the moment of connecting-up to the vascular access device. A further circumstance reducing the risk of contamination is that the priming liquid supply line can be connected to the extracorporeal circuit in the priming process and remains connected to the circuit up until the end of the blood return process after treatment (for the operativity of the system the fluid connection to the source can be opened or closed using a clamp). The reduction of risk of contamination is also due to the fact that the totality or almost-totality of the extracorporeal blood remaining in the circuit at the end of the treatment can be returned to the patient without there being any need for disconnecting the arterial line from the vascular access, as will be better explained during the description that follows.

A further advantage of the invention is that during a recirculation of the filling liquid during the priming process, the whole extracorporeal blood circuit can be involved in the rinsing process of the recirculating liquid.

These aims and advantages and more besides, which will better emerge from the description that follows, are attained by a filling process and a filling device according to one or more of the accompanying claims.

Further characteristics and advantages of the present invention will better emerge from the detailed description that follows, of at least a preferred embodiment of the invention, illustrated by way of non-limiting example in the accompanying figures of the drawings.

BRIEF DESCRIPTION OF THE DRAWINGS

The description will follow herein below, with reference to the figures of the drawings, provided as a non-limiting example and in which.

DETAILED DESCRIPTION

Figure 1:
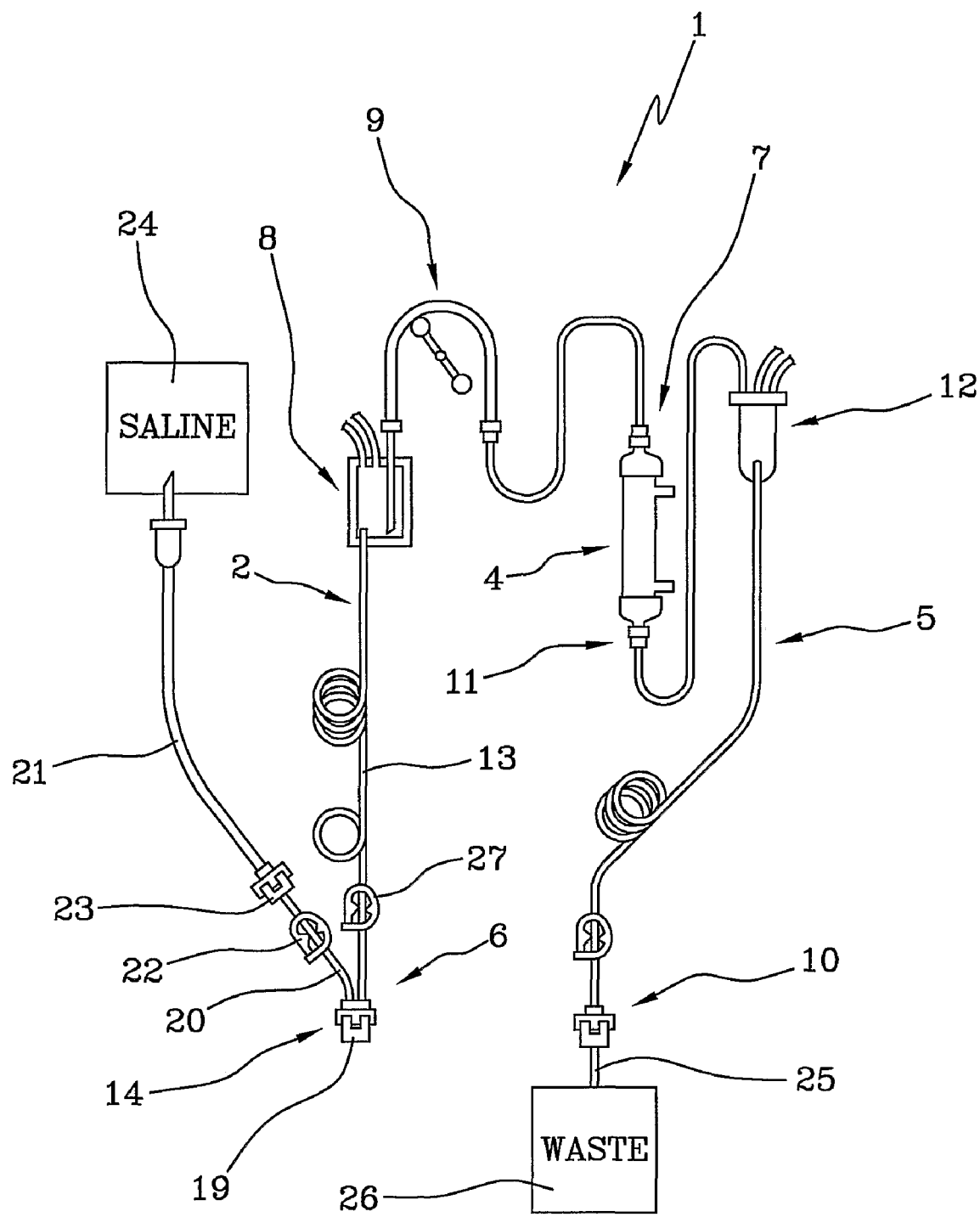
FIG. 1 is a blood set according to the invention, in a priming configuration.

With reference to the above-cited figures of the drawings, 1 denotes in its entirety a blood set for an extracorporeal blood treatment (for example a dialysis treatment). The blood set 1, which is used for extracorporeal blood circulation, comprises an arterial line 2 which, during the treatment, removes the blood from a vascular access 3 of a patient (see FIG. 2) and leads it to a blood treatment device 4 (for example a dialyser), and a venous line 5 which takes the treated blood from an outlet of the treatment device 4 and returns it to the patient. The blood treatment device is, for example, a membrane exchanger provided with a semipermeable membrane which separates a blood compartment from a fluid compartment.

The arterial line 2 comprises a patient end 6 destined for connection with the vascular access 3 of the patient and a device end 7 destined for connection with the blood treatment device 4. The arterial line 2 comprises an arterial blood chamber 8 for air-liquid separation. The arterial line 2 also comprises a pump segment 9 destined for coupling with a blood pump (for example a rotary peristaltic pump). The arterial line 2 also comprises various other elements, such as for example: an anti-coagulant infusion line (arranged upstream or downstream of the pump segment 9); a blood access site for removal/injection (generally of a type having a soft wall which a needle can penetrate and arranged upstream or downstream of the pump segment 9); a sterile liquid infusion point (for example a substitution liquid in a hemo(dia)filtration treatment); at least a sensor of arterial pressure (for example a deformable membrane which is sensitive to pressure or a transducer-protector on a service line); one or more service lines in communication with the upper part of the arterial blood separation chamber 8 or with other points of the arterial line 2; a tract which is predisposed to be coupled with a hematic concentration sensor (for example an infra-red sensor), and so on.

The venous line 5 also comprises a patient end 10 destined to connect to the vascular access 3 of the patient, and a device end 11 destined to be connected with the blood treatment device 4. The venous line 5 comprises a blood chamber 12 for air-liquid separation. The patient end 10 of the venous line terminates with a male luer connector for sealed removable connection with a known-type vascular access device (see FIG. 2). Before use the male luer connector is closed by a removable cap (of known type and not illustrated). The venous line 5 is further provided with various elements normally present in a venous line, such as for example: a blood access site for removal/injection (generally of a type having a soft wall which a needle can penetrate and arranged upstream of the venous separation chamber 12); a sensor of venous pressure (for example a deformable membrane which is sensitive to pressure or a transducer-protector on a service line); one or more service lines in communication with the upper part of the venous blood separation chamber 8 or with other points of the venous line 2; a filter arranged at a blood outlet of the venous separation chamber 12; an infusion point for a sterile liquid (for example a substitution liquid in a hemo(dia)filtration treatment); a tract which is predisposed to be coupled with a hematic concentration sensor (for example an infra-red sensor), and so on.

Figure 3:
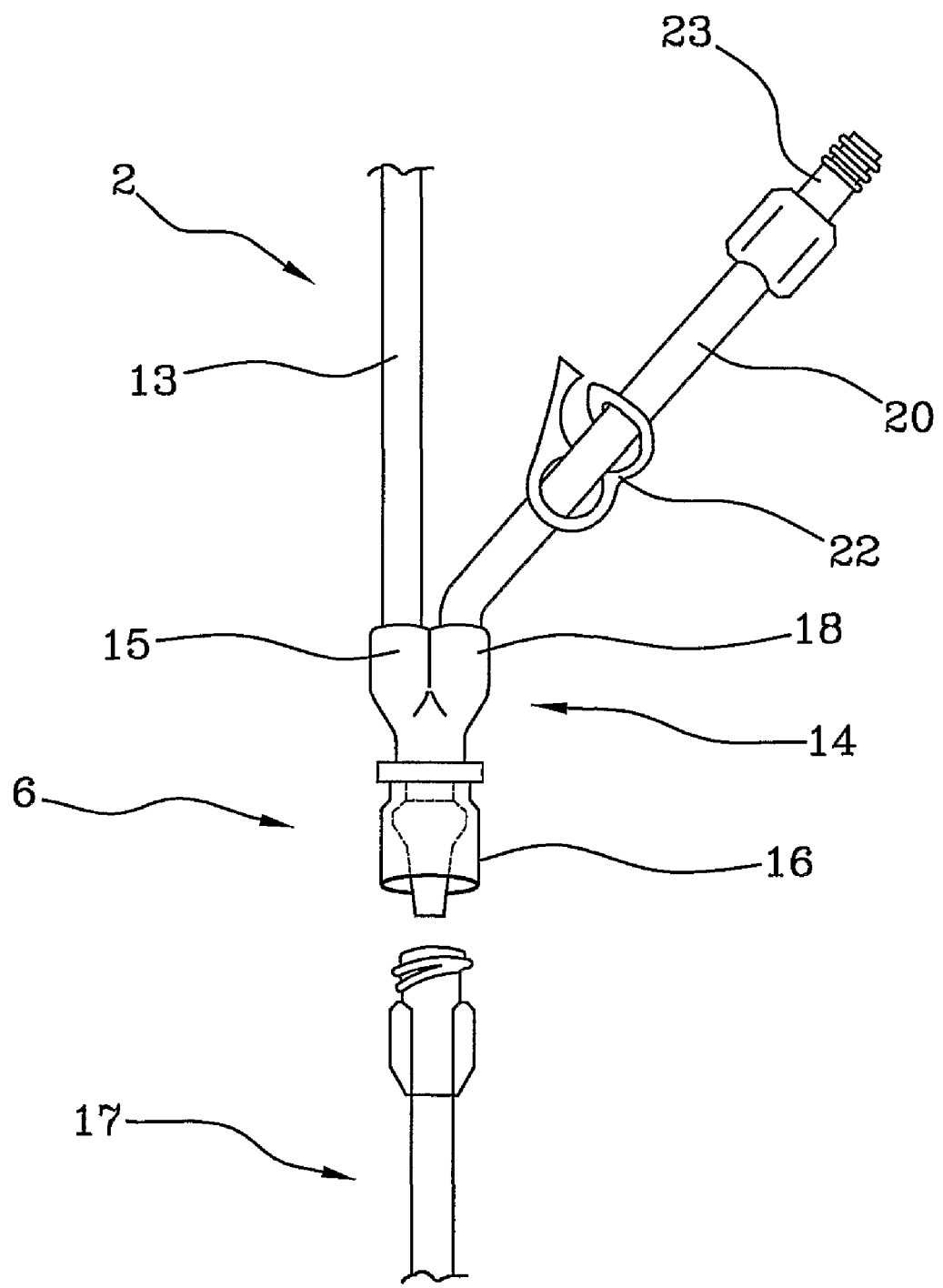
FIG. 3 is an enlarged detail of the arterial patient end of the blood set of FIG. 1.

The patient end 6 of the arterial line 2 is illustrated in greater detail in FIG. 3.

The arterial line 2 comprises a blood transport tube 13 made of a flexible plastic material (for example soft PVC) where the main flow of extracorporeal blood flows during treatment. The patient end 6 of the arterial line 2 comprises a multi-port connector 14 having at least three ports in which: a first port 15 is connected to an end of the blood transport tube 13; a second port 16 is suitable for connection with a vascular access device 17 in a treatment configuration (see FIG. 2); and a third port 18 is included for inlet of a sterile liquid constituted in particular by a physiological liquid, for example saline, used as a priming liquid.

The first port 15 comprises a tubular connection in which a portion of end of the blood transport tube 13 is inserted. The end portion is solidly joined with a known-type fluid seal, for example by gluing or welding, to a tubular wall of the first port 15 of the multi-port connector.

Figure 2:
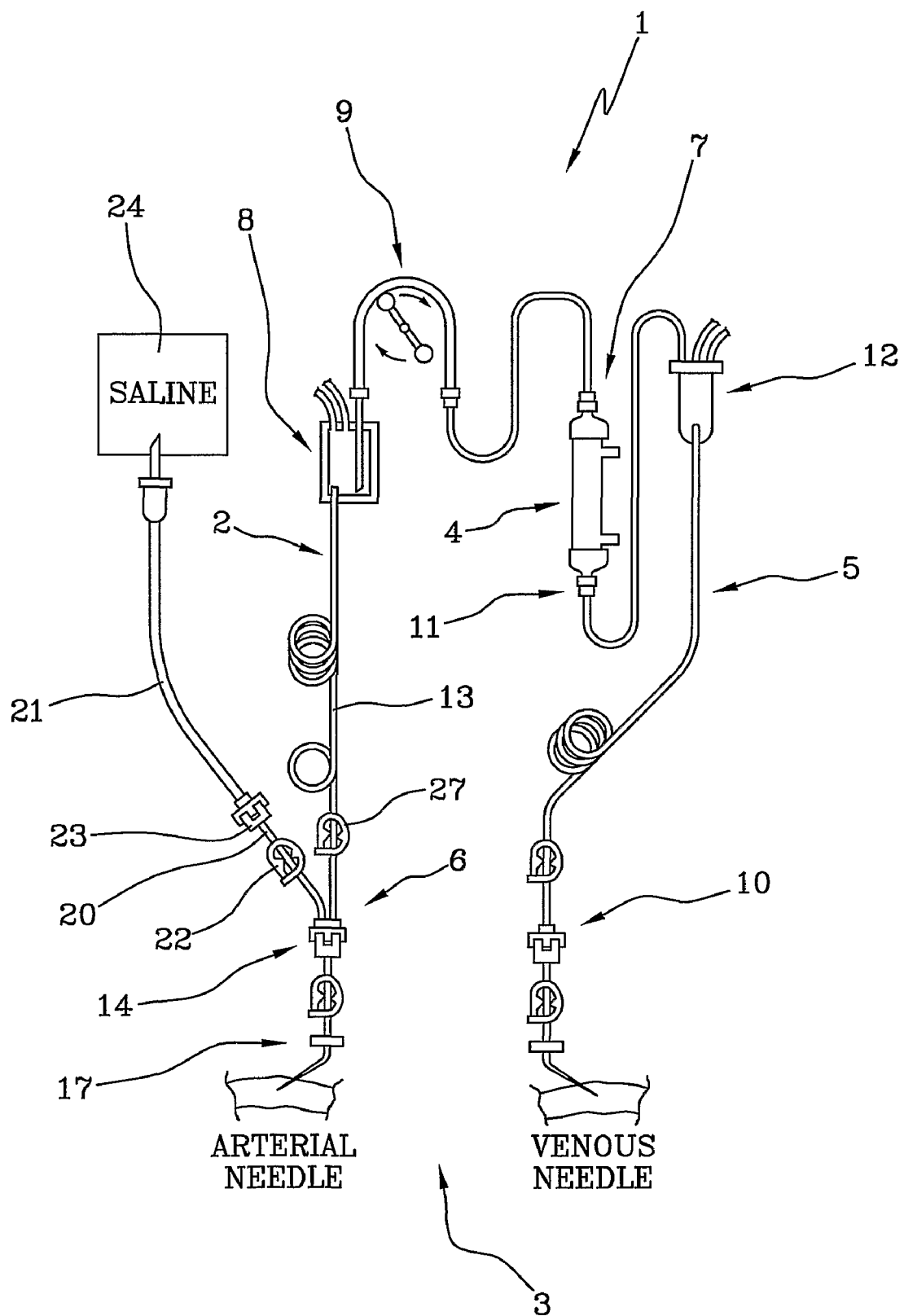
FIG. 2 is the blood set of FIG. 1 at the end of an extracorporeal blood treatment session.

The second port 16 comprises a luer connector for connecting up to a corresponding seating of a vascular access device 17 of known type (usually provided with a needle or a catheter which can be introduced into the vascular system of the patient or donor). Normally the luer connector associated to the arterial line 2 is a male connector, while the seating associated to the vascular access device is female. In FIG. 2 (treatment configuration), the second port 16 connector is shown coupled to the seating of the vascular access device 17, while in the enlarged view of FIG. 3 the connector and seating are shown uncoupled. The second port 16 is further provided with a removable cap 19 which is schematically shown in FIG. 1 (priming configuration) and which is removed before connection of the arterial line 2 to the vascular access (as will be better explained herein below).

The third port 18 is connected to a first end of a service tube 20 having a second end which is opposite the first and which is connectable to a supply line 21 of a priming liquid. The service tube 20 is provided with a closure clamp 22, which in the illustrated embodiment is a luer connector 23, for connecting-up with the supply line 21 of the priming liquid. Before use the luer connector 23 of the service tube is closed by a removable cap (of known type and not illustrated). In the priming configuration (FIG. 1) the priming liquid supply line is coupled to the service tube 20 at one end and to a priming liquid source (a bag of saline 24) at the opposite end.

In an embodiment of the invention (not illustrated) the priming liquid supply line is directly connectable to the third port of the multi-port connector. In this case the third port comprises a connector, for example a luer connector (female) which is predisposed to connect with a seating (male luer) borne on the priming liquid supply line. The priming liquid supply line can be provided with a clamp (manual) for interrupting the liquid supply.

Returning to the illustrated embodiment, the multi-port connector 14 has a Y conformation, in which the second port 16 is arranged at an opposite end from the first port 15 and the third port 18.

The first port 15 has a longitudinal access which corresponds to the coupling axis between the tubular connector of the first port 15 and the end of the blood transport tube 13 of the arterial line 2 inserted sealedly in the tubular connector. The second port 16 has a longitudinal axis that corresponds to the coupling axis between the second port 16 (luer connector) and the vascular access device 17 (luer seating). The third port 18 has a longitudinal axis which corresponds to the coupling axis between the tubular connector of the third port 18 and the end of the priming liquid line tube end 21 inserted sealedly (by welding, gluding or any other known system for stable sealed coupling) in the tubular connector. In the embodiment in which the third port comprises a connector (female luer), the longitudinal axis of the third port coincides with the connector coupling axis.

The longitudinal axis of the third port 18 has an inclination which forms a greater-than-right angle with the inclination of the longitudinal axis of the second port 16. Further, the longitudinal axis of the third port 18 has an inclination which forms a smaller angle than a right-angle with the inclination of the longitudinal axis of the first port 15. In the illustrated embodiment the longitudinal axis of the third port 18 is also coplanar with the longitudinal axis of the second port 16, and is also coplanar with the longitudinal axis of the third port 18. Furthermore, in the embodiment the longitudinal axis of the third port 18 has the same inclination as the longitudinal axis of the first port 15 (thus the two longitudinal axes of the first port 15 and the third port 18 form a null angle). Also, in the embodiment the longitudinal axis of the third port 18 has an opposite inclination with respect to the longitudinal axis of the second port 16 (thus the two longitudinal axes of the second port 16, and the third port 18 form a 180° angle). The two longitudinal axes of the second port 16 and the third port 18 form an angle comprised between about 90° and 180° circa.

The multiport connector 14 comprises a press-formed piece made of plastic, bearing the first port 15, the third port 18 and at least a part of the second port 16, in particular a part bearing a luer cone. The multiport connector 14 further comprises a second piece bearing a rotating part of a male luer connector in the form of an internally threaded jacket, and a third piece constituted by the removable closure cap 19 of the male luer connector.

Before use for extracorporeal blood circulation during a treatment, the above-described blood set 1 is emptied of air and filled with liquid using a priming process which is described herein below.

The device end 7 of the arterial line 2 and the device end 11 of the venous line 5 are connected to the blood treatment device 4, in particular the blood chamber of the treatment device (dialyzer). The device end 7 of the arterial line 2 can be connected to the upper connection of the device 4, while the device end 11 of the venous line 5 can be connected to the lower connection thereof (as shown in FIG. 1), or vice versa. The patient end 10 of the venous line 5 is connected to a discharge. The connection can comprise the connection of the connector (luer, for example female) of the patient end 10 of the venous line 5 with a seating (for example a luer male connector) connected to a discharge conduit 25 (as in the illustrated embodiment). The discharge can comprise a collection bag 26 (as in the illustrated embodiment), or an open container, or a drainage tube of a machine for extracorporeal blood treatment connected to an outlet of the fluid chamber of the blood treatment device 4.

The pump segment 9, which in this case is part of the arterial line 2, is connected to the blood pump of the extracorporeal blood treatment apparatus.

The third port 18 of the multiport connector 14 is connected to a priming liquid source, which in the preferred embodiment comprises the saline bag 24. The connection involves removing the removable cap closing and protecting the luer connector 23 on the end of the service tube 20 connected to the third port 18. The connector 23 at the end of the service tube 20 is then connected to a seating (a male luer) borne at an end of the supply line 21 of the priming liquid. The line 21 is fluidly connected to the source of priming liquid (saline bag 24); the connection is made in a known way, for example by a perforating element on the supply line 21 which is introduced into a priming liquid container.

The priming liquid is made to flow after the clamps obstructing the passage are removed (the clamps arranged on the service tube 20, the arterial line 2, the venous line 5) and after starting up the blood pump which circulates the liquid. The liquid flows from the priming liquid source to the third port 18 and then from the third port 18 to the first port 15, and thereafter from the first port 15 to the blood treatment device 4, passing along the blood transport tube 13. It then fills the blood chamber of the blood treatment device 4 and runs along the venous line 5 up until it reaches the discharge 26. During the filling stage of the extracorporeal blood circuit with the priming liquid, the air contained in the circuit is expelled there-from.

During the priming procedure, the second port 16 of the multiport connector 14 is closed by the removable cap 19, which is usually included in the protective package thereof prior to use. This has the advantage of limiting the risk of contamination of the extracorporeal circuit, and also limits the number of operations needed to ready the extracorporeal circuit before treatment. The second port 16 is opened at the end of the priming procedure to enable connection of the extracorporeal blood circuit to the vascular access (FIG. 2). Thanks to the special conformation of the multiport connector 14, in which the third port 18 for inletting the priming liquid and the other ports (the first port 15 and the second port 16) for blood passage are integrated into a single element and are arranged close to one another, the priming procedure is done simply, rapidly, logically and reliably. At the end of the priming procedure it is possible that a small amount of air remains inside the second port 16, in particular inside the cone of the male luer connector. However the presence if any of such a small quantity of trapped air can be acceptable; it would in fact be so negligible as not to lead to any risk to the patient or donor, but would be released, for example, into one of the air-liquid separation chambers (more probably into the arterial chamber 8) at the start of the treatment, when the blood removed from the patient starts flowing in the arterial line 2, without reaching the venous vascular access and without significantly changing the level of liquid in the chamber.

The priming procedure can include, in some cases, a stage in which the priming liquid is recirculated along the whole extracorporeal circuit. The patient arterial end (in particular the second port 16 of the multiport connector) is connected to the patient venous end so as to form a closed loop, after which the blood pump is activated so that the circuit filling liquid is made to circulate along the closed loop for a certain period of time. Thanks to the multiport 14 connector, this recirculation stage can interest the whole extracorporeal blood circuit.

During the extracorporeal treatment (FIG. 2) the saline source can remain connected to the extracorporeal circuit and, if necessary, is ready for infusion into the extracorporeal blood by opening the clamp 22 on the service tube 20.

At end of treatment the saline source 24 and the relative supply line 21 can be used for the return procedure to the patient or donor of the extracorporeal blood remaining in the circuit, following a termination procedure for an extracorporeal blood treatment, described herein below.

At end of treatment (FIG. 1) the blood set 1 is full of blood and the second port 16 of the multiport connector is connected to the vascular access of the patient or donor. At this point, after having stopped the blood pump, the connection between the second port 16 of the multiport connector is closed, as is the patient vascular access, for example by closing the clamp normally located on the arterial vascular access 17 (see FIG. 2). The third port 18 of the multiport connector is then fluidly connected with the saline solution source 24, for example by opening the clamp 22 of the service tube 20, then the blood pump is activated to return the blood to the patient through the venous vascular access. In this way the saline is also aspirated and flows from the source 24 to the third port 18, from the third port 18 to the first port 15 and from the first port 15 to the blood treatment device 4, passing along the arterial line 2 and then, after crossing the blood chamber of the blood treatment device 4, flowing along the venous line 5. When the separation line between blood and saline nears the venous vascular access, the blood pump is stopped and via a series of known operations not described herein, the extracorporeal circuit is detached from the patient. Thanks to the special conformation and arrangement of the multiple connector 14, during the blood return stage to the patient the saline enters the extracorporeal circuit practically at the patient end, with a consequent simplification and reduction of the operations to be carried out. Furthermore the blood return stage can be completed before the arterial line is disconnected from the arterial vascular access, with a considerable reduction of the risk of contamination. During the termination procedure of the blood treatment, where the majority of the extracorporeal blood is returned to the patient, the stage of causing the saline to flow from the third port 18 to the first port 15 (so that the blood can be returned via the venous vascular access) can be preceded by a further stage of causing the saline to flow from the third port 18 to the second port 16, and from the second port 16 to the vascular access device 17; in this case the saline flow can be realised by force of gravity, by placing the source 24 of saline high up. This final stage, normally preliminary to other stages of the blood return procedure, returns to the patient the quantity of blood contained in the vascular access device 17 through the arterial vascular access. During this further stage the connection between the first port 15 and the blood treatment device 4 is interrupted, for example by closing a clamp 27 operating on the arterial line 2.

The invention claimed is:

1. A priming procedure of a blood set, the blood set comprising a blood transport tube having a patient end which is connectable to a vascular access and a device end which is connectable to a blood treatment device, wherein the patient end comprises a multiport connector having a first port which is connected to the blood transport tube, a second port which is suitable for connecting to a vascular access device, and a third port for inlet of a priming liquid, and wherein the second port comprises an integral luer connector and being configured to be coupled to a removable cap, the priming procedure comprising stages of:
    connecting the third port of the multiport connector to a source of a priming liquid;
    making the priming liquid flow from the source to the third port, from the third port to the first port, and from the first port to the blood transport tube.

2. The priming procedure of claim 1, comprising stages of connecting the device end to a blood treatment device and of causing the priming liquid to flow from the first port to the blood treatment device passing through the blood transport tube.

3. The priming procedure of claim 1, wherein the second port is closed by a removable closure element.

4. The priming procedure of claim 1, wherein the stage of causing the priming liquid to flow comprises a stage of activating a blood pump which blood pump is coupled to a tract of the blood transport tube.

5. A procedure for terminating an extracorporeal blood treatment, carried out by means of a blood set, the blood set comprising a blood transport tube having a patient end which is connectable to a vascular access and a device end which is connectable to a blood treatment device, wherein the patient end comprises a multiport connector having a first port which is connected to the blood transport tube, a second port which is suitable for connecting to a vascular access device, and a third port for inlet of a priming liquid, and wherein the second port comprises an integral luer connector and being configured to be coupled to a removable cap,
    the blood set being full of blood, the second port of the multiport connector being connected to the patient, the procedure comprising stages of:
        closing the connection between the second port of the multipart connector and the patient;
        fluidly connecting the third port of the multiport connector with a source of a physiological solution;
        causing the physiological solution to flow from the source to the third port, from the third port to the first port and from the first port to the blood treatment device passing through the blood transport tube, to return the blood to the patient.

6. The procedure of claim 5, wherein the stage of closing the connection between the second port of the multipart connector and the patient comprises closing a clamp in a vascular access device interpositioned between the second port and the patient.

7. The procedure of claim 5, wherein the stage of causing the physiological solution to flow comprises opening a clamp interpositioned between the third port and a source of the physiological solution, and activating a blood pump coupled to the blood transport tube.

8. The procedure of claim 5, comprising a further stage of causing the physiological solution to flow from the third port to the second port, and from the second port to the vascular access device.

9. The procedure of claim 8, wherein during the further stage the connection of the first port to the blood treatment device is closed.

* * * * *